United States Patent
Børgesen

(10) Patent No.: US 10,625,060 B2
(45) Date of Patent: Apr. 21, 2020

(54) SHUNT DEVICE AND A METHOD FOR SHUNTING CEREBROSPINAL FLUID

(71) Applicant: CSF-DYNAMICS A/S, Kongens Byngby (DK)

(72) Inventor: Svend Erik Børgesen, Kokkedal (DK)

(73) Assignee: CSF-DYNAMICS A/S, Kgs. Lyngby (DK)

( * ) Notice: Subject to any disclaimer, the term of this patent is extended or adjusted under 35 U.S.C. 154(b) by 0 days.

(21) Appl. No.: 16/290,753

(22) Filed: Mar. 1, 2019

(65) Prior Publication Data
US 2019/0192834 A1 Jun. 27, 2019

Related U.S. Application Data

(63) Continuation of application No. 16/309,083, filed as application No. PCT/EP2017/065153 on Jun. 20, 2017.

(51) Int. Cl.
*A61M 27/00* (2006.01)
*A61M 25/04* (2006.01)

(52) U.S. Cl.
CPC .......... *A61M 27/006* (2013.01); *A61M 25/04* (2013.01); *A61M 2202/0464* (2013.01)

(58) Field of Classification Search
CPC .......... A61M 25/04; A61M 2202/0464; A61M 27/006
See application file for complete search history.

(56) References Cited

U.S. PATENT DOCUMENTS

| | | |
|---|---|---|
| 2,969,066 A | 1/1961 | Holter et al. |
| 3,233,610 A | 2/1966 | Wade |
| 3,566,875 A | 3/1971 | Stoehr |
| 3,583,387 A | 6/1971 | Garner et al. |
| 3,894,541 A | 7/1975 | El-Shafei |
| 4,182,343 A | 1/1980 | Inaba |
| 4,377,169 A | 3/1983 | Banks |
| 4,382,445 A | 5/1983 | Sommers |
| 4,438,773 A | 3/1984 | Letterio |
| 4,500,311 A | 2/1985 | Redmond et al. |
| 4,578,057 A | 3/1986 | Sussman |
| 4,605,395 A | 8/1986 | Rose et al. |
| 4,646,752 A | 3/1987 | Swann et al. |

(Continued)

FOREIGN PATENT DOCUMENTS

| | | |
|---|---|---|
| JP | 2004-508109 A | 3/2004 |
| WO | 98/11934 A1 | 3/1998 |

(Continued)

OTHER PUBLICATIONS

International Search Report and Written Opinion for PCT/EP2017/065153, dated Sep. 29, 2017.

(Continued)

*Primary Examiner* — Leslie R Deak
(74) *Attorney, Agent, or Firm* — Merchant & Gould P.C.

(57) ABSTRACT

A shunt device for shunting cerebrospinal fluid (CSF) from a CSF containing space to a sinus system cavity comprises a tubular inlet element, a flow restricting part, and a tubular outlet element having an outlet end with an outlet opening for insertion in the sinus system cavity, and a one-way valve preventing flow in a direction from the outlet opening to the inlet opening. The shunt device further comprises a distancer, said distancer being provided at the outlet end of the tubular outlet element.

29 Claims, 7 Drawing Sheets

(56) References Cited

U.S. PATENT DOCUMENTS

| | | | |
|---|---|---|---|
| 4,781,673 | A | 11/1988 | Watanabe |
| 4,781,674 | A | 11/1988 | Redmond et al. |
| 4,784,648 | A | 11/1988 | Singh et al. |
| 4,903,707 | A | 2/1990 | Knute et al. |
| 4,904,236 | A | 2/1990 | Redmond et al. |
| 5,000,731 | A | 3/1991 | Wong et al. |
| 5,042,974 | A | 8/1991 | Agarwal |
| 5,054,497 | A | 10/1991 | Kapp et al. |
| 5,891,100 | A | 4/1999 | Fleckenstein |
| 5,980,480 | A | 11/1999 | Rubenstein et al. |
| 6,264,625 | B1 | 7/2001 | Rubenstein et al. |
| 6,283,934 | B1 | 9/2001 | Børgesen |
| 6,383,159 | B1 | 5/2002 | Saul et al. |
| 6,689,085 | B1 | 2/2004 | Rubenstein et al. |
| 6,905,474 | B2 | 6/2005 | Børgesen |
| 7,025,742 | B2 | 4/2006 | Rubenstein et al. |
| 7,118,548 | B2 | 10/2006 | Børgesen |
| 7,172,571 | B2 | 2/2007 | Moskowitz et al. |
| 7,169,160 | B1 | 6/2007 | Middleman et al. |
| 7,309,330 | B2 | 12/2007 | Bertrand et al. |
| 8,257,296 | B2 | 9/2012 | Bertrand et al. |
| 8,292,856 | B2 | 10/2012 | Bertrand et al. |
| 8,298,168 | B2 | 10/2012 | Bertrand et al. |
| 8,333,728 | B2 | 12/2012 | Bertrand et al. |
| 8,672,871 | B2 | 3/2014 | Heilman et al. |
| 9,199,067 | B2 | 12/2015 | Heilman et al. |
| 9,387,311 | B1 | 7/2016 | Heilman et al. |
| 9,545,505 | B2 | 1/2017 | Heilman et al. |
| 9,662,479 | B2 | 5/2017 | Heilman et al. |
| 9,669,195 | B2 | 6/2017 | Heilman et al. |
| 9,724,501 | B2 | 8/2017 | Heilman et al. |
| 9,737,696 | B2 | 8/2017 | Heilman et al. |
| 9,737,697 | B2 | 8/2017 | Heilman et al. |
| 10,058,686 | B2 | 8/2018 | Heilman et al. |
| 10,112,036 | B2 | 10/2018 | Heilman et al. |
| 10,307,576 | B2 | 6/2019 | Heilman et al. |
| 10,307,577 | B2 | 6/2019 | Malek et al. |
| 2007/0112291 | A1 | 5/2007 | Børgesen |
| 2007/0112293 | A1 | 5/2007 | Børgesen |
| 2010/0191168 | A1 | 7/2010 | Heilman |
| 2013/0103026 | A1 | 4/2013 | Kleshinski et al. |
| 2014/0207179 | A1 | 7/2014 | Farhangnia et al. |
| 2015/0080854 | A1 | 3/2015 | Spiel et al. |
| 2016/0136398 | A1 | 5/2016 | Heilman et al. |
| 2017/0209676 | A1 | 7/2017 | Heilman et al. |
| 2018/0015267 | A1 | 1/2018 | Heilman et al. |
| 2018/0207412 | A1 | 7/2018 | Malek et al. |
| 2018/0256866 | A1 | 9/2018 | Malek et al. |
| 2018/0264240 | A1 | 9/2018 | Heilman et al. |
| 2019/0298977 | A1 | 10/2019 | Heilman et al. |

FOREIGN PATENT DOCUMENTS

| | | |
|---|---|---|
| WO | 00/48642 A2 | 8/2000 |
| WO | 02/07811 A1 | 1/2002 |
| WO | 02/15955 A2 | 2/2002 |
| WO | 02/20083 A2 | 3/2002 |
| WO | 2005/051474 A2 | 6/2005 |
| WO | 2015/108917 A1 | 7/2015 |
| WO | 2016/070147 A1 | 5/2016 |

OTHER PUBLICATIONS

International Search Report and Written Opinion for PCT/EP2016/064145, dated Feb. 23, 2017.

M.J. Albeck, M.D. et al., "Age dependency of resistance to cerebrospinal fluid outflow", J Neurosurg 89: 275-278 (1998).

M.J. Albeck, M.D. et al., "Intracranial pressure and cerebrospinal fluid outflow conductance in healthy subjects", J Neurosurg 74: 597-600 (1991).

S.E. Børgesen, M.D. et al., "Cerebrospinal fluid conductance and compliance of the craniospinal space in normal-pressure hydrocephalus", J Neurosurg 51: 521-525 (1979).

S.E. Børgesen, "Conductance to Outflow of CSF in Normal Pressure Hydrocephalus", Acta Neurochirurgica 71: 1-45 (1984).

S.E. Børgesen et al., "The Predictive Value of Confuctance to Outflow of CSF in Normal Pressure Hydrocephalus", Brain 105: 65-86 (1982).

S.E. Børgesen, M.D. et al., "Relationships between intracranial pressure, ventricular size, and resistance to CSF outflow", J Neurosurg 67: 535-539 (1987).

F. Gjerris et al., "Current Concepts of Measurement of Cerebrospinal Fluid Absorption and Biomechanics of Hydrocephalus", Advances and Technical Standards in Neurosurgery 19: 145-177 (1992).

Office Action for Japanese Patent Application No. 2018-567619, dated Jun. 4, 2019.

Report from 2018 Annual Meeting, The Society of University Neurosurgeons, Houston, TX (Mar. 22-25, 2018).

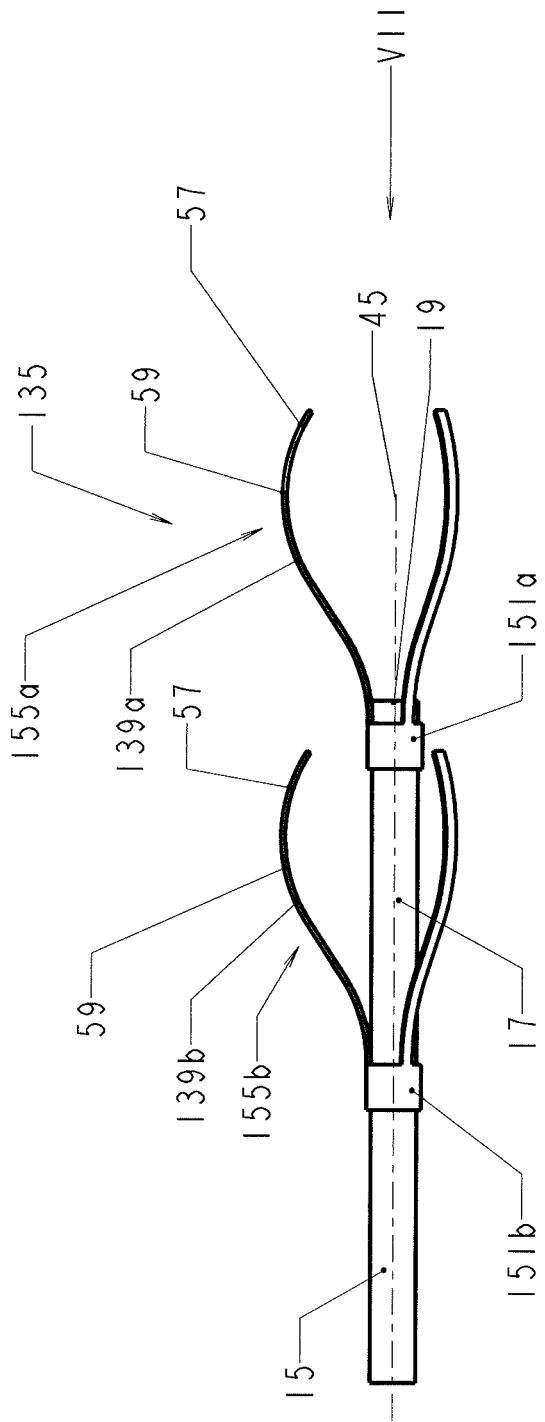

SHUNT DEVICE AND A METHOD FOR SHUNTING CEREBROSPINAL FLUID

This is a Continuation Application of U.S. patent application Ser. No. 16/309,083, which is a National Stage Application of International Application No. PCT/EP2017/065153, filed Jun. 20, 2017, which claims the benefit of priority to European Application No. PCT/EP2016/064145, filed in on Jun. 20, 2016, and which applications are incorporated herein by reference. To the extent appropriate, a claim of priority is made to each of the above disclosed applications.

TECHNICAL FIELD OF THE INVENTION

The present invention relates to an improved shunt device for shunting cerebrospinal fluid (CSF) from the subarachnoid space to vena jugularis, or to sinus transversus, in order to relieve hydrocephalus.

More specifically, the invention relates to a shunt device comprising a tubular outlet element having an outlet end with an outlet opening adapted for insertion in a sinus system cavity, such as sinus transversus or vena jugularis.

The shunt device comprises a distancer for keeping the outlet end of the tubular outlet element away from endothelial tissue by making sure that the outlet end of the tubular outlet element is maintained during use of the shunt at a certain minimum distance from endothelium surrounding said tubular outlet element.

Preferably no contact is made between the outlet end of the tubular outlet element and the endothelium. The distancer may be forming an integral part of the outlet end of the tubular outlet element.

The invention also relates to a method for shunting cerebrospinal fluid using the improved shunt device according to the present invention.

BACKGROUND

The brain and spinal cord are encased in the cranium and vertebral column inside a thin membrane known as the meninges. The space within the meninges includes, among others, the ventricles, and CSF is produced in the chorioid plexus in the ventricles at a rate of 0.3-0.4 ml/min under normal conditions.

CSF flows through the ventricles, aqueduct and basal cisterns over the cerebral surface to the arachnoid villi, from where the CSF is absorbed into the sagittal sinus (including sinus transversus). However, in subjects suffering from hydrocephalus, CSF drainage is hindered, and CSF shunting is required to provide a sufficient drainage.

Prior art shunt devices have a relatively short lifespan due to multiple factors, including e.g. obstruction of the drain, and shunt deficiencies resulting e.g. in excess drainage of CSF.

Obstruction of a shunt device may be complete, partial, or intermittent. If the obstruction is only partial or intermittent, an individual may experience periodic headaches, nausea and vomiting, drowsiness, listlessness, loss of appetite, and a general decrease in mental functioning.

Complete obstruction of a shunt device may cause the same symptoms, as well as more severe signs of blurred vision, loss of coordination, and possible loss of consciousness.

Obstruction may be a consequence of an encapsulation of the shunt device in the form of endothelialization of the shunt outlet by endothelial tissue, which envelops around the outlet, and forms a barrier capable of impairing or arresting drainage.

Overdrainage often results when CSF is shunted to the peritoneal cavity when the pressure difference between the inlet and the outlet ends of some prior art shunts is too high. The difference in pressure results in very low, or even negative, intracranial pressure, and this may in turn result in a collapse of the ventricles, or even subarachnoidal effusion of blood and subdural haematoma.

Several attempts have been made to alleviate the above-cited problems, including the provision of a surface coating, as explained in US 2007/0112291A1. However, even though use of a surface coating may in some cases provide an improvement, most shunt devices in use today still have to be replaced within 5 years of insertion.

WO 2015/108917 discloses a shunt device and methods for fixing the shunt device directly to a wall of the sinus system during use. WO 2015/108917 does not teach or suggest a shunt device having a distancer for maintaining a certain minimum distance between an outlet end of a tubular outlet element and endothelium surrounding said tubular outlet element, preferably without making any contact with said endothelium.

There is a need for shunt devices which may be inserted over longer periods of time, and which are less likely to be obstructed as a result of contact between elements of the shunt device and surrounding tissue, including endothelial tissue of the sinus system, including vena jugularis.

SUMMARY OF THE INVENTION

One object of the present invention is to provide a shunt device as disclosed herein which is less likely to be obstructed by endothelial tissue.

Accordingly, in a first aspect, the present invention provides a shunt device comprising a tubular inlet element (7) having an inlet end (9) with an inlet opening (11) for insertion into a cerebrospinal fluid (CSF) containing space (13) of an individual, and a tubular outlet element (15) having an outlet end (17) with an outlet opening (19) adapted for insertion in a sinus system cavity (21).

The above-mentioned tubular elements (7, 15) comprise an inner lumen extending through the respective tubular elements. The inner lumen of tubular inlet element (7) and the inner lumen of tubular outlet element (15) are operably connected to allow for CFS to flow through the shunt device in a direction from the inlet opening (7) to the outlet opening (19).

The shunt device comprises a distancer for avoiding tissue contact between the shunt and surrounding tissue, and for maintaining the outlet end (17) of the tubular outlet element (15) at an essentially fixed distance from any endothelium tissue surrounding said tubular outlet element.

Neither the distancer nor the tubular outlet element (15) are fixated to endothelial tissue, including tissue of vena jugularis, and neither the distancer nor the tubular outlet element (15) are penetrating endothelial tissue under practical circumstances when the shunt device is positioned in a sinus system cavity.

At least the outlet end of the tubular outlet element should be maintained at a predetermined distance from said endothelium, preferably with no contact, or the least possible contact, with said endothelium.

The predetermined distance may be the overall longest distance it may be possible to attain at any time during insertion of the shunt device between the outlet end of the tubular outlet element and any surrounding tissue of a sinus system cavity into which the shunt device is inserted.

In other words, it is preferred to maintain the outlet end of the tubular outlet element as far away from surrounding endothelial tissue as possible, and it is more preferred to avoid any contact at all between the outlet end of the tubular outlet element and surrounding tissue of a sinus system cavity, including vena jugularis.

Examples of cerebrospinal fluid (CSF) containing spaces include, but are not limited to, the subarachnoid space of a brain ventricle. A sinus system cavity include, but is not limited to, sinus transversus and vena jugularis.

The shunt device according to the invention preferably also comprises a flow restricting part (31) positioned between the inlet opening (9) and the outlet opening (19), and the shunt device according to the present invention preferably also comprises a one-way valve (33) preventing flow in a reverse direction, i.e. in a direction from the outlet opening to the inlet opening.

Accordingly, it is an object of the present invention to provide a shunt as described herein comprising a distancer for maintaining the outlet end of a tubular outlet element at a predetermined or fixed distance from endothelium surrounding said tubular outlet element, preferably with no contact, or with the least possible contact, between said outlet end of the tubular outlet element and said endothelium.

A "fixed or predetermined distance" is defined herein is a distance which creates no obstruction, or at least substantially no obstruction, of the shunt device over time when the shunt is in use, such as over a period of at least five years, preferably at least seven years.

In a second aspect, the present invention relates to a method for shunting cerebrospinal fluid using a shunt device according to the first aspect of the invention, the method comprises the steps of:
  a) inserting at least a part of the inlet end of the tubular inlet element, comprising the inlet opening, into the subarachnoid space of a subject,
  b) inserting at least a part of the outlet end of the tubular outlet element, comprising the outlet opening and the distancer in a compacted state into the sinus transversus or the vena jugularis cavity of the subject,
  c) changing the state of the distancer from the compacted state to an expanded use state, and
  d) fixating the shunt device.

DETAILED DESCRIPTION OF THE INVENTION

The distancer of the shunt device maintains the outlet end of the tubular outlet element of the shunt device at a predetermined distance from endothelium tissue surrounding the tubular outlet element.

It is preferred that no contact, or the least possible contact, is made with the surrounding endothelium tissue, such as endothelium tissue of vena jugularis.

Preferably, the outlet end of the tubular outlet element is maintained substantially at a central position of, or at the center of, a sinus system cavity, including vena jugularis, in which the shunt device is positioned.

The outlet end of the tubular outlet element is preferably also maintained in a position at least substantially parallel to the flow direction of the sinus system cavity, including vena jugularis, in which the shunt device is positioned.

Additionally preferred, the outlet end of the tubular outlet element is maintained in a position at least substantially parallel to the central longitudinal axis of the shunt device.

The distancer is preferably provided at the outlet end of the tubular outlet element, and it is preferred that the distancer is integrated with the tubular outlet element so as to form an integral part of said tubular outlet element.

The distancer may comprise at least two, such as at least three distance keepers each being positioned at a distance from the tubular outlet element in a direction perpendicular to a central longitudinal axis of the tubular outlet element under practical circumstances of using the shunt device.

The distancer, preferably provided at or on the outlet end of the tubular outlet element, keeps the outlet end of the tubular outlet element at a distance, preferably a maximum distance, i.e. as long a distance as possible, away from the inner walls of the cranial sinus system cavity into which the shunt device is inserted.

The distance keeping exerted by the distancer serves the purpose of ensuring the there is no contact, or only a minimal contact, with surrounding tissue, thereby preventing any undesirable contact with the endothelium tissue of the inner wall of e.g. the vena jugularis, and thereby in turn considerably reducing the risk of endothelium overgrowth, and hence subsequent obstruction, of the CSF draining portions of the shunt device.

The term "distancer" is to be understood as an element which is provided on or at the outlet end of the tubular outlet element with the objective of establishing and maintain over time a distance, such as a maximum distance, between the outlet end of the tubular outlet element and surrounding endothelium tissue.

The distancer and the outlet end of the tubular outlet element preferably form an integrated unit of the shunt device, as compared to separate entities capable of being connected to each other, but only connected to each other during use of the shunt device under practicable circumstances.

Using a distancer e.g. with two or three spaced apart distance keepers, i.e. individual distance keepers arranged at one or more than one predetermined distance from each other in tangential direction relative to the central longitudinal axis, also serves to provide a higher degree of stability of the inserted shunt device, while at the same time at least minimizing, and preferably preventing, movement of the tubular outlet element of the shunt device relative to the surrounding endothelial tissue. In this way, the outlet end of the tubular outlet element of the shunt device is maintained at an overall maximum distance from all endothelial tissue immediately surrounding the outlet end of the tubular outlet element of the shunt device.

Preferably, the distancer is preventing the outlet end of the tubular outlet element from being moved towards tissue of a sinus system cavity wall. The number of distance keepers, and the physical size of each distance keeper, should be designed so as to not interfere, or to interfere only minimally, with the passage of fluid through the cavity in which the shunt device is inserted.

Distance keepers are preferably determined as points of the most protruding parts of the distancer in directions away from the central longitudinal axis. It is to be understood that the preferably at least two or three distance keepers are defined as the at least two or three portions of the distancer protruding farthest away from the central longitudinal axis in respective different directions.

When more than e.g. three portions of the distancer are protruding equally far from the central longitudinal axis, it is to be understood that more than three distance keepers form part of the shunt device.

The central longitudinal axis is preferably straight, but need not be straight, and a straight longitudinal axis is preferably defined by a central axis of the tubular outlet element, and/or it may be defined by a central axis of the inner lumen of the shunt device.

In order to eliminate or keep the risk of overgrowth to a minimum, the distancer and/or distance keepers of the distancer are preferably embodied with a smooth surface, which provides the lowest possible friction with the inner cavity wall of a sinus system.

For the same reason, the dimensions of the distancer in the expanded use state of the shunt device is preferably selected so that the distancer does not press against the inner cavity wall when inserted into the sinus system cavity.

It is preferred to provide a distancer having distance keepers that are not in any substantial contact with an inner cavity wall of a sinus system during steady state use of the shunt device, but essentially only serves as "bumpers", aimed at keeping secure distances, including secure minimum distances, between the outlet opening of the tubular outlet element and a sinus system cavity wall.

Secure minimum distances may e.g. be maintained during changes in e.g. the flow through the cavity. However, the flow restricting member of the shunt device serves as a structure capable of maintaining an essentially constant flow of cerebrospinal fluids through the tubular elements. It is presently preferred that the restriction value is less than 8 mm Hg/ml/min.

In an embodiment of the present invention, the distancer is compactable into a compacted state, and expandable into at least one expanded use state in which where the at least two or three distance keepers protrude further from the central longitudinal axis than in the compacted state.

It is to be understood, that a force is needed to compress the distancer into the compacted state, which exceeds the normal forces experienced by the distancer when the distancer has been inserted in a sinus system cavity. Thus, the distancer will not be compressed into the compacted state, unless intentional force is applied, such as by an intended retraction of the distancer from the sinus system cavity.

In one embodiment, each distance keeper forms part of a distance member protruding from the tubular outlet element in a direction away from the central longitudinal axis. Each distance member may include one or more distance keepers, and different distance members may have different numbers of distance keepers, as long as the total number of distance keepers is at least two or three.

In another embodiment of the invention, at least two or three distance keepers are positioned equidistantly from each other at least in a use state of the shunt device. This positioning allows for a distribution of the at least two or three distance keepers which is sufficient for maintaining a predetermined minimum distance between the outlet of the tubular outlet element and surrounding epithelium during use. In one embodiment, an equidistant distribution of distance keepers is achieved by an equidistant distribution of the distance members.

In one embodiment of the invention, when at least three distance keepers and/or distance members are employed, the at least three distance keepers and/or distance members are positioned in a fashion satisfying the equation $\alpha+\beta+\gamma=360°$, where $\alpha$, $\beta$, and $\gamma$ represents non-overlapping angles relative to the central longitudinal axis between two distance keepers and/or distance members, as seen in the direction of the central longitudinal axis of the inner lumen.

Preferably, $\alpha>90°$, $\beta>90°$, and $\gamma>90°$, and equally preferably $\alpha<150°$, $\beta<150°$, and $\gamma<150°$. This arrangement of distance keepers and/or distance members allows for a distribution between distance keepers and/or distance members, which is sufficient to provide a suitable minimum distance between the outlet opening of the tubular outlet element and surrounding endothelium during practical use of the shunt device.

In one embodiment of the invention, the distancer comprises connector members each capable of interconnecting both distance members, or interconnecting two or more of the at least three distance members, in order to reduce or hinder tangential or circumferential movement of the distance members in the direction of the central longitudinal axis.

The distance members are preferably able to move substantially only in a tangential direction, if all distance members are moving. Thus, the distancer may comprise parts aimed at substantially maintaining angles between the at least two or three distance members, so that they do not move closer to each other, or further away from each other, in a tangential direction during use, as seen from the central longitudinal axis.

Accordingly, the at least two or three distance members may move towards each other in a radial direction, as seen from the central longitudinal axis, during contraction into the compacted state, and they may move further away from each other during expansion into an expanded state.

In an embodiment of the present invention, the distancer comprises an expandable, resilient mesh comprising e.g. the at least three distance keepers defining the maximum protrusion of the mesh from the central longitudinal axis.

By providing a distancer comprising a mesh, a more resilient structure of the distancer is achieved, and this in turn provides more stability, which may be preferred in some cases. The mesh should be sufficiently coarse so that it does not significantly impair the passage of fluids when the shunt device is in use.

The distancer of the present invention may be provided with one or more than one set of distance members, where the distance members of each set is arranged to protrude from the tubular outlet element at different distances from the outlet opening in the direction of the central longitudinal axis.

If each set of distance members comprise e.g. at least three distance members, this will provide an increased stability to the distancer, but any number of distance members, including two, may be provided, and different sets may have a different number of distance members, and each distance member may include the same or a different number of distance keepers.

Providing at least two sets of distance members each set comprising at least three distance keepers distributed around the central longitudinal axis either substantially equidistantly, or e.g. defined by the afore-mentioned angles $\alpha$, $\beta$, and $\gamma$, will maintain the outlet end of the tubular outlet element substantially at a central position or at the center of a sinus system cavity in which the shunt device is positioned.

Preferably, the outlet end of the tubular outlet element is maintained substantially at a central position of, or at the center of, a sinus system cavity in which the shunt device is positioned.

The outlet end of the tubular outlet element is preferably maintained in a position at least substantially parallel to the flow direction of the sinus system cavity in which the shunt device is positioned.

Additionally preferred, the outlet end of the tubular outlet element is maintained in a position at least substantially parallel to the central longitudinal axis of the shunt device.

Different sets of distance members may be attached to the tubular outlet element at different distances from the outlet opening of the tubular outlet element.

Each set of distance members of the distancer may protrude substantially equally, or differently, with regard to a distance from the central longitudinal axis, and with regard to the direction of protrusion.

It is possible to attach each distance member separately to the tubular outlet element, but at present, it is believed that an interconnection of distance members resulting e.g. from the provision of three or more of the distance members as a set with a common attachment to the tubular outlet element, will provide an advantageous stability to the distancer.

The distancer, or one or more distance members, may be connected to the tubular outlet element via one or more attachment members.

The distancer may comprise a part extending into the inner lumen of the tubular outlet element such that said part provides a constriction of the inner lumen thereby acting as the flow restricting member. Thus the flow restricting part or a flow restricting member may be provided as a part of the distancer.

Either all or part of i) the internal or external surface of a shunt body, or part thereof, including the distancer, or ii) all or part of the internal or external surface of a brain ventricle catheter, or iii) all or part of the internal or external surface of a sinus catheter, can comprise a biocompatible and/or hemocompatible material comprising an inert surface preventing biological material from maintaining longer lasting contact with the inert surface, and/or comprising a hemocompatible surface coated with a plurality of charged species capable of increasing the hemocompatibility of the surface.

The internal or external surface of the shunt body, including the distancer, or the internal or external surface of the brain ventricle catheter, or the internal or external surface of the sinus catheter, can comprise a biocompatible and/or hemocompatible material comprising an inert surface preventing biological material from maintaining longer lasting contact with the inert surface, and/or comprise a polymer material coated with a plurality of charged species capable of increasing the hemocompatibility of the surface.

In one embodiment, the internal or external surface of the shunt body comprises a biocompatible and/or hemocompatible material comprising an inert surface preventing biological material from maintaining longer lasting contact with the inert surface, wherein the hemocompatible material can comprise a polymer material coated with a plurality of charged species capable of increasing the hemocompatibility of the surface.

In a further embodiment, the internal or external surface of the brain ventricle catheter also comprises a biocompatible and/or hemocompatible material comprising an inert surface preventing biological material from maintaining longer lasting contact with the inert surface, wherein the hemocompatible material can comprise a polymer material coated with a plurality of charged species capable of increasing the hemocompatibility of the surface.

In a still further embodiment, the internal or external surface of the sinus catheter also comprises a biocompatible and/or hemocompatible material comprising an inert surface preventing biological material from maintaining longer lasting contact with the inert surface, wherein the hemocompatible material can comprise a polymer material coated with a plurality of charged species capable of increasing the hemocompatibility of the surface.

The hemocompatible surface coated with a plurality of charged species capable of increasing the hemocompatibility of the surface can be e.g. a silicone elastomer, teflon, HD polyethylene, such as gas sterilized polypropylene, polysulfone, polystyrene, PVC, nylon, titanium, shape memory alloys such as Nitinol or polyethersulfone. The charged species can be e.g. polyethylene glycols or another macromolecule having a molecular weight of less than e.g. 20,000. The hemocompatible surface is in one embodiment a modified polymer surface as disclosed in PCT/DK00/00065 and/or PCT/DK01/00557.

The internal or external surfaces of the shunt device are preferably sterilisable. It is preferred that one or more of said surfaces act as an effective diffusion barrier preventing ions from the shunt entering the body and protecting the shunt from attack by the biological environment.

In another preferred embodiment of the present invention, one or more of said surfaces, including the surfaces of the distanced, are non-adhesive. In another preferred embodiment, one or more of said surfaces are non-toxic. In another preferred embodiment, one or more of said surfaces are non-immunogenic.

In one preferred embodiment of the present invention, said biocompatible and/or hemocompatible material comprises diamond like carbon (DLC) or the like. Equally preferably, said biocompatible and/or hemocompatible material can comprise a turbostratic carbon, more preferably pyrolytic carbon.

In another preferred embodiment of the present invention, said biocompatible and/or hemocompatible material comprises a ceramic. Said ceramic is preferably titanium nitride (TiN), or the like. In another preferred embodiment, said biocompatible and/or hemocompatible material comprises phosphatidyl choline di-ester. In another preferred embodiment, said biocompatible and/or hemocompatible material comprises a Sputtered carbon coating, such as Graphit-iC, or the like.

In another preferred embodiment, said biocompatible and/or hemocompatible material comprises Teflon, and the like. In another embodiment of the present invention, said biocompatible and/or hemocompatible material comprises a calcification-resistant biocompatible material.

In one preferred embodiment, the surface is the external surface of the sinus catheter. In another preferred embodiment, the surface is the internal surface of the sinus catheter.

The distancer of the shunt device is preferably made of a resilient or pseudo-elastic material, such as e.g. a nickel titanium alloy (Nitinol).

In a second aspect, the present invention relates to a method for shunting cerebrospinal fluid using a shunt device according to the first aspect of the invention, the method comprises the steps of:
 a) inserting at least a part of the inlet end of the tubular inlet element, comprising the inlet opening, into the subarachnoid space of a subject,
 b) inserting at least a part of the outlet end of the tubular outlet element, comprising the outlet opening and the distancer in a compacted state into the sinus transversus or the vena jugularis cavity of the subject,
 c) changing the state of the distancer from the compacted state to an expanded use state, and
 d) fixating the shunt device.

The insertion of the shunt device may be carried out through any suitable entrance point, known to the person skilled in the art.

In an embodiment of the present invention, the insertion of at least a part of the outlet end of the tubular outlet element and the distancer in a compacted state, is carried out through an opening in the vena jugularis.

In an embodiment, the shunt device is fixated in a position where the distancer is at a distance of at least 3 cm along the central longitudinal axis from the opening forming the entry point into the vena jugularis.

If another entry point is used, the shunt device is preferably fixated in a position, so that the distancer is at least 3 cm away from the entry point to the cavity into which the distancer is inserted.

By fixating the shunt device in a position where the distancer is at a distance of at least 3 cm from the entry point into the cavity wherein the distancer is inserted, the risk of endothelium growing over the outlet of the tubular outlet element is minimal.

A third aspect of the present invention relates to the use of a shunt device according to the first aspect of the present invention in the treatment of hydrocephalus.

The shunt device may, however, also be used in the treatment of other diseases including Alzheimer's disease and other diseases caused by toxic substances in the CSF as discussed in US 2007/0112293 A1 (Borgesen), which is incorporated herein in its entirety by reference.

SHORT DESCRIPTION OF THE DRAWINGS

In the following, exemplary embodiments of the device, the method, and the use according to the invention will be described with reference to the schematic drawings in which:

FIG. 6 is a side view of the outlet end with two sets of distancer members in another embodiment of the invention;

DETAILED DESCRIPTION OF THE DRAWINGS

Figure 1:
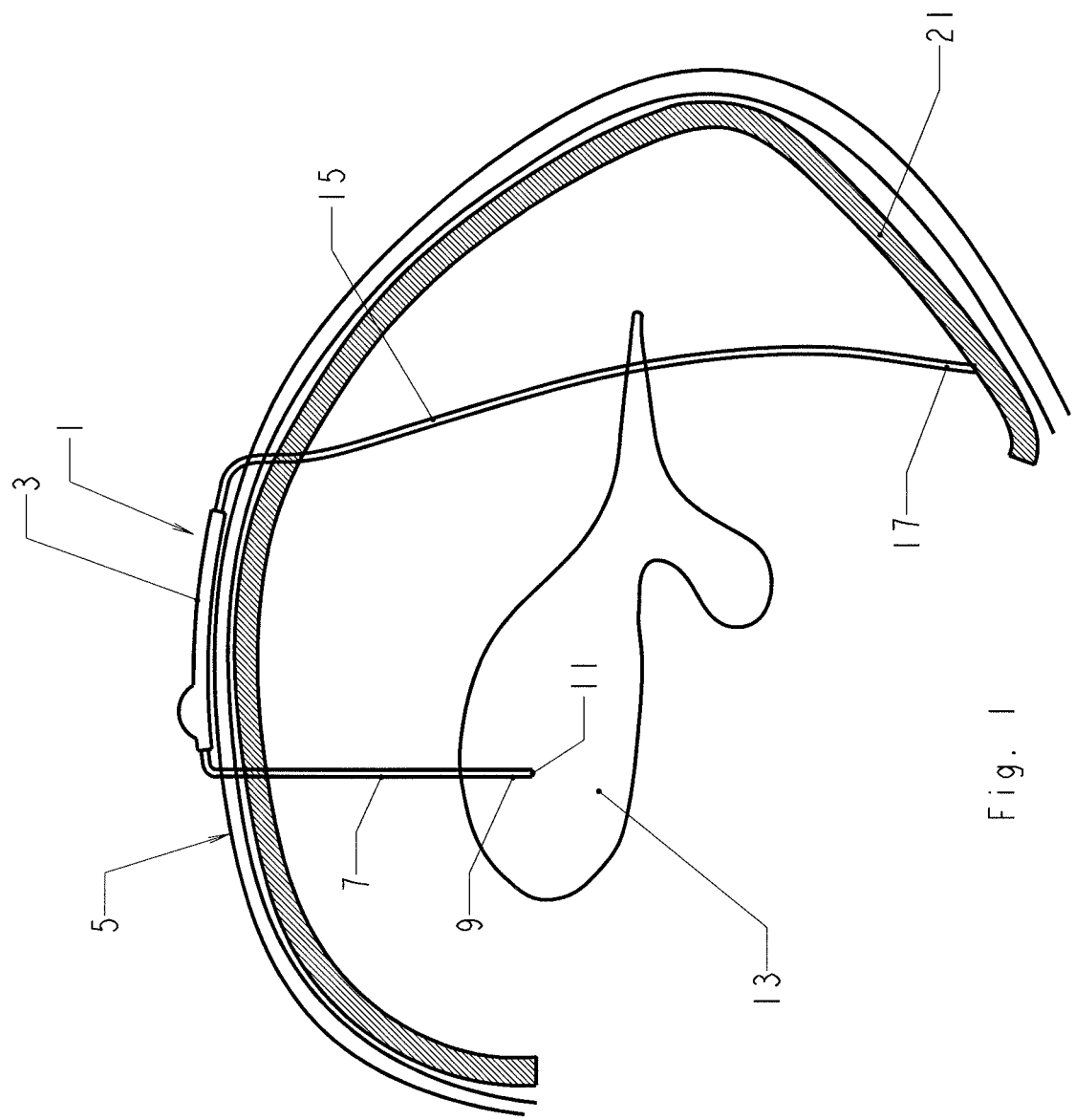
FIG. 1 shows a schematic picture of a shunt device installed in a patient.

FIG. 1 shows a shunt device according to an embodiment of the present invention installed in a patient.

The shunt device (1) comprises a shunt body (3) which is positioned subcutaneously on top of the calvarium (5) of the patient.

A tubular inlet element (7), constituting a brain ventricle catheter, is connected to a first end of the shunt body (3). The tubular inlet element (7) comprising an inlet end (9) with an inlet opening (11), which is inserted into a CSF containing space (13) from which it is desired to drain CSF, such as the subarachnoid space or a brain ventricle.

A tubular outlet element (15) is connected to another, opposite end of the shunt body (3. The tubular outlet element (15) comprises an outlet end (17) with an outlet opening (19) (see FIG. 3). The outlet end (17) is inserted in a cavity of the sinus system (21) of the patient, e.g. in sinus transversus or in vena jugularis, the outlet element thus constituting a sinus catheter.

Figure 2:
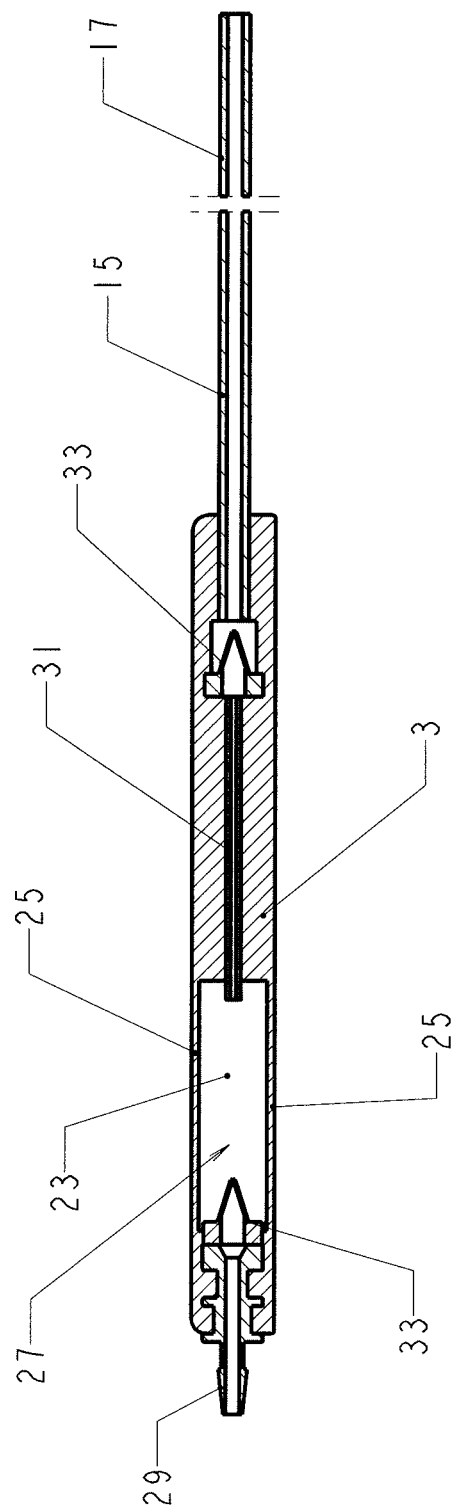
FIG. 2 shows a part of the shunt device of FIG. 1.

FIG. 2 shows a preferred embodiment of the shunt body (3), preferably made from silicone rubber, comprising an antechamber (23) having opposite flat walls (25), preferably made from hard silicone rubber, and opposite domed walls (27), preferably made from soft, perforatable, self-healing silicone rubber. Preferably, at the first end which is an inlet end of the shunt body (3), the antechamber's walls end in a tapering end comprising a tip (29), to which the brain ventricle catheter or tubular inlet element (7) can be connected and secured.

The shunt body further comprises a flow restricting member (31) provided by a tubular flow restricting part of the shunt body (3). Preferably, the antechamber (23) is connected to the tubular flow restricting part so that an outlet end of the antechamber (23) forms an inlet to the tubular flow restricting part, i.e. the flow restricting member (31).

Preferably, a check valve or non-return valve, i.e. a one-way valve (33) is arranged both at the entrance to the antechamber (23) and at an outlet of the flow restricting member (31). Preferably, said one-way valves do not have any inherent resistance or opening pressure, and essentially do not exert any resistance on the flow of cerebrospinal fluid from the brain ventricle catheter through the shunt body (3) to the sinus catheter i.e. the outlet element (15).

In preferred embodiments of the present invention, fluidic connection to a sinus system cavity of the patient is provided by the tubular outlet element (15), which is attached to the shunt body (3) at the end thereof opposite the tip (29), and fluidic connection to a brain ventricle of the patient is provided by the tubular inlet member (7) or brain ventricle catheter which is preferably attached to the tip (29), which is provided with an annular bead, and the tubular inlet member is optionally secured by means of a ligature.

Preferably, the length of the tip (29) is about 5 mm. In one preferred embodiment of the present invention, the tubular flow restricting member (31) is dimensioned in accordance with Hagen-Poiseulle's law so as to provide a passive and substantially constant resistance to flow of less than 8 mm Hg/ml/min.

In preferred embodiments an internal radius, R, of an inner lumen of the tubular flow restricting part constituting the flow restricting member (31) is more than 0.05 mm and preferably less than 0.50 mm, and appropriate lengths, L, of the flow restricting member (31) can be calculated accordingly, as follows:

$$L=((ICP-P_{ss})\times \pi \times R^4)/(8\times F\times V) \quad \text{(Hagen-Poiseuille's law)},$$

wherein ICP is the intracranial pressure, $P_{ss}$ is the pressure in the sagittal sinus, F is the flow rate of the cerebrospinal fluid and V is the viscosity of the cerebrospinal fluid. In preferred embodiments, the length of the flow restricting part is in the range of from about 3.0 mm to about 90 mm.

The shunt device described so far of the present invention is embodied and used e.g. as disclosed in US 2007/0112291 A1, which is incorporated herein by reference.

Figure 3:
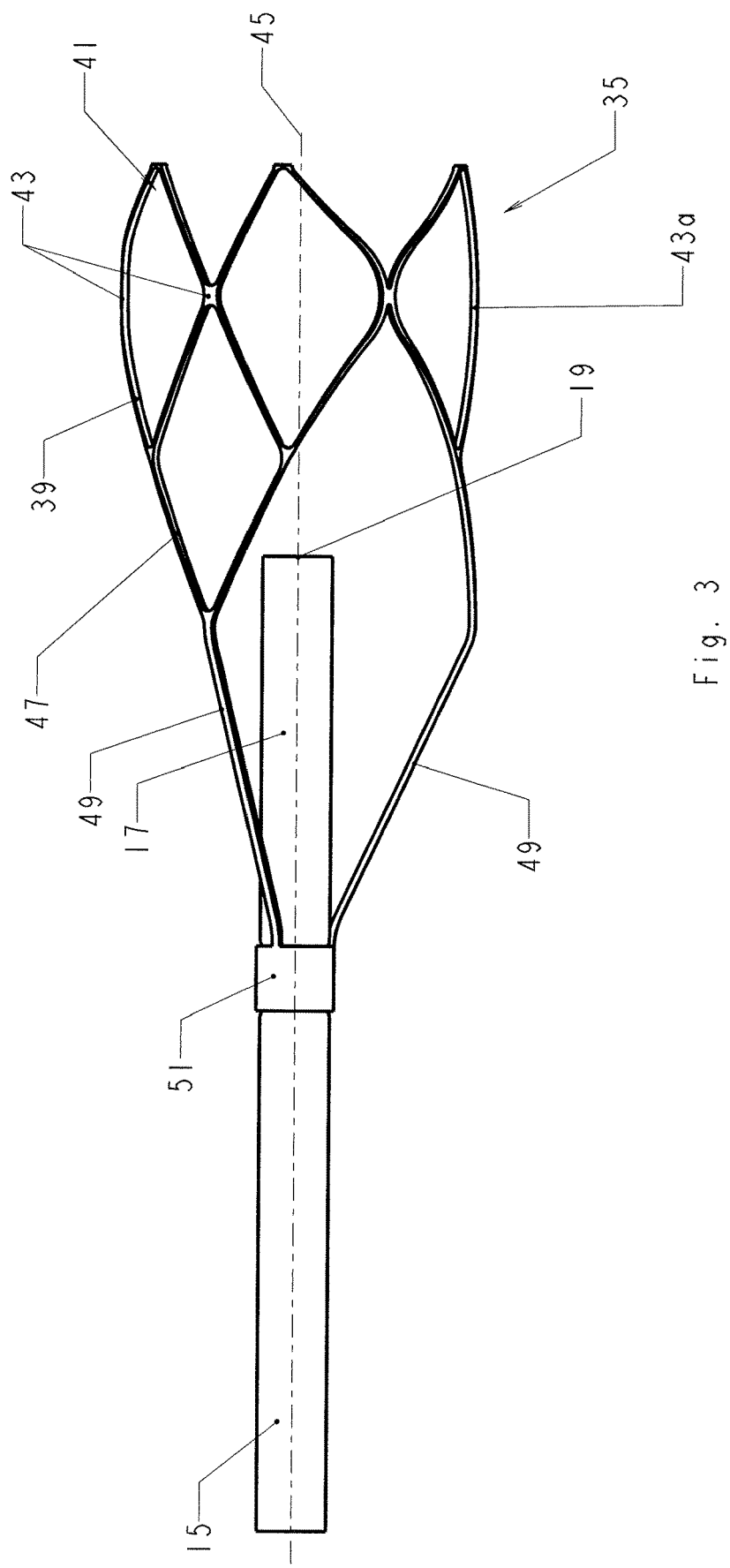
FIG. 3 shows an outlet end of the shunt device of FIG. 2 comprising a distancer in an embodiment of the invention.
Figure 4:
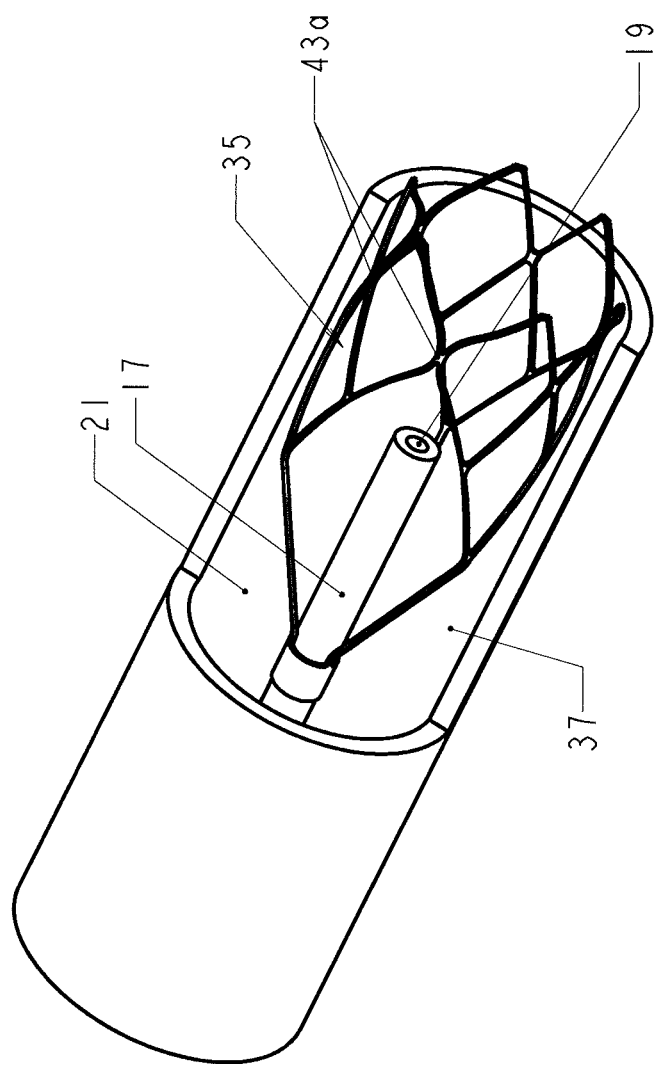
FIG. 4 shows the outlet end of FIG. 3 in a vessel.

Referring to FIGS. 3 and 4, according to the present invention the outlet end (17) of the tubular outlet element (15) of FIG. 2 is provided with a distancer (35) for keeping the outlet end (17) with the outlet opening (19) a minimum distance from the inner surface of a wall (37) of a vessel or cavity of the sinus system in which the outlet end is positioned and thus to keep the outlet end (17) at a minimum distance from the endothelium of said wall (37).

In the embodiment shown in FIGS. 3 and 4 the distancer (35) comprises a distance member (39) formed as a resilient mesh comprising a first set of six loops (41) mutually interconnected at connections (43) to respective adjacent loops thus forming a ring of loops encircling a central longitudinal axis (45) extending through and out from the tubular outlet element (15).

Of the six loops (41), only three are seen in FIG. 3 the other three being hidden behind the three loops being actually seen. The resilient mesh further comprises a second set of three loops (47) each of which is connected through a branch (49) with an attachment member (51) by which the distancer (35) is connected to the tubular outlet element (15).

In an expanded use state of the distance member (39), the connections (43) are positioned furthest from the central longitudinal axis (45) extending though and out from the tubular outlet element (15) and the connections (43) constitutes distance keepers (43a) of the distancer (35).

Thus in the present embodiment shown in FIGS. 3 and 4, six distance keepers are provided and they are placed circumferentially in a substantially equidistant manner around the central longitudinal axis (45).

As it is best seen in FIG. 4 the distancer (35) will keep the outlet end (17) with the outlet opening (19) at a minimum distance from the inner surface of the wall (37). In the embodiment shown the distancer (35) does not span the width of the cavity or vessel in which it is positioned and accordingly only a few, if any, of the distance keepers or connections (43) are actually in contact with the inner surface of the wall (37). It is however possible within the present invention that the distancer (35) does span said width.

Figure 5:
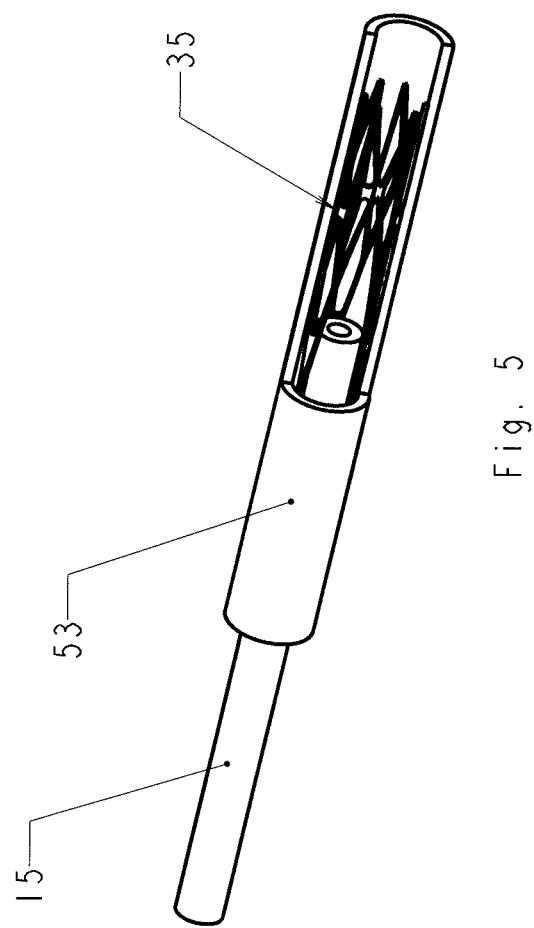
FIG. 5 shows the outlet end of FIG. 3 in an introducer sheet.

For insertion of the tubular outlet element (15) in a cavity or vessel of a patient the distancer (35) is, as shown in FIG. 5 compacted and introduced together with the outlet end (17) of the tubular outlet element (15) into an introducer sheet (53). Such procedure will in general be familiar to the skilled person.

Thus in a method for shunting cerebrospinal fluid using the shunt device (1) steps to be performed are
a) inserting at least a part of the inlet end (9) of the tubular inlet element (7), comprising the inlet opening (11), into a CSF containing space, such as the subarachnoid space of a patient,
b) inserting at least a part of the outlet end (17) of the tubular outlet element (15), comprising the outlet opening (19) and the distancer (35), said part of the outlet end (17) and the distancer (35) being accommodated in an introducer sheet (53) for the distancer to be in a compacted state, into a cavity (21) of the sinus system such as the sinus transversus or the vena jugularis cavity of the patient,
c) changing the state of the distancer from the compacted state to an expanded use state by withdrawing the introducer sheet (53), and
d) fixating the shunt device (1).

The insertion of the shunt device may be carried out through any suitable entrance point, known to the person skilled in the art.

Such methods are to be considered as anticipated by the present invention.

In an embodiment the insertion of at least a part of the outlet end (17) of the tubular outlet element (15) and the distancer (35) in the introducer sheet (53), is carried out through an opening in the vena jugularis.

In an embodiment, the shunt device is fixated in a position where the distancer (35) is at a distance of at least 3 cm along the central longitudinal axis (45) from the opening forming the entry point into the vena jugularis. If another entry point is used, the shunt device is preferably fixated in a position, so that the distancer is at least 3 cm away from the entry point to the cavity (21) into which the distancer (35) is inserted. By fixating the shunt device (1) in a position where the distancer (35) is at a distance of at least 3 cm from the entry point into the cavity (21) wherein the distancer (35) is inserted, the risk of endothelium growing over the outlet end (17) and the outlet opening (19) of the tubular outlet element (15) is minimal.

The shunt device (1) having been installed may be used to relieve hydrocephalus and drain CSF and possible toxic substances in the CSF that for some reason is not drained naturally. Thus the shunt device may apart from treating hydrocephalus, be used for treating clinical conditions such as e.g. Alzheimer's disease. Treatment of Alzheimer's disease is an example of a clinical condition capable of being treated by using the shunts of the invention to drain CSF comprising e.g. amyloid plaque proteins from the CSF space of a patient.

In addition to Alzheimer's disease, the shunt device according to the present invention will also be useful in treating other conditions resulting from the accumulation of toxic substances and resulting lesions in the patient's brain, such as e.g. Down's Syndrome, hereditary cerebral hemorrhage with amyloidosis of the Dutch Type (HCHWA-D), epilepsy, narcolepsy, Parkinson's disease, polyneuropathies, multiple sclerosis, amyotrophic lateral sclerosis (ALS), myasthenia gravis, muscular dystrophy, dystrophy myotonic, other myotonic syndromes, polymyositis, dermatomyositis, brain tumors, Guillain-Barre-Syndrome, and the like, as disclosed in US 2007/0112291 A1 and US 2007/0112293 A1, both of which are incorporated herein by reference.

As further disclosed in US 2007/0112291 A1, the methods disclosed herein are also envisaged as being used in combination with other medical treatments, for instance conventional drug treatments.

By "in combination", it is meant that the methods disclosed herein may be used on an individual prior to, during, or after treatment of the individual with one or more other medical treatment.

Said medical treatment may comprise administration of a compound inside the inner lumen of said shunt device. In one preferred embodiment, an individual is treated with the methods disclosed herein, in combination with administration of one or more of an antibiotic, anti-coagulants such as heparin, Acetazolamide or Frusemide, Isosorbide, Glycerol, Urokinase, calcification inhibiting agents or MEDTA. In another, equally preferred embodiment, a patient is treated with the methods disclosed herein, in combination with administration of one or more of an anti-infective compound such as e.g. vancomycin, EDTA, Gentamycin, Chymotrypsin, chlorine dioxide, or Minocycline. It is also envisaged that the shunt system of the present invention may be adapted to be capable of being infused with a drug, thus allowing ease of drug delivery. The shunt device may also be impregnated with bioactive compounds, such as a drug, before being positioned inside the patient.

Figure 7:
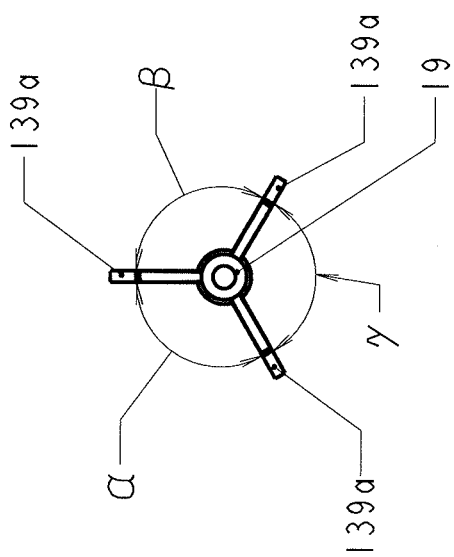
FIG. 7 is a view in direction of arrow VII in FIG. 6.

FIGS. 6 and 7 show a second embodiment of a distancer (135) according to the present invention comprising two sets (155a) and (155b) of distance members (139a) and (139b) wherein the distance members (139a) of the first set (155a) are attached to a first attachment member (151a) and the distance members (139b) of the second set (155b) are attached to a second attachment member (151b). The attachment members (151a and (151b) are mounted of the outlet end (17) of the tubular outlet element (15) at the outlet opening (19). Each set (155a) and (155b) comprise three distance members (139a) and (139b), respectively and apart from mounting the respective sets (155a) and (155b) the attachment members (151a) and (151b) constitute connector members connecting and retaining the mutual positions of the respective distance members (139a) and (139b). Alternatively the distance members might each be mounted on the tubular outlet element by means of respective attachment members (not shown).

In the latter case independent connector members might be provided for retaining the mutual positions of the distance members. As seen in FIG. 7 the distance members (139a) (and the distance members (139b) which are hidden behind the former) are positioned with mutual angular distances α, β and γ each of angles α, β and γ being 120°.

The distance members (139a) and (139b) are each shaped to have a curved part (57) defining the maximum protrusion of the respective distance member (139a) and (139b) the curved parts (57) thus constituting the distance keepers (59) of the respective distance members (139a) and (139b).

The two sets (155a) and (155b) of distance members are positioned at different distances from the outlet opening (19) along the central longitudinal axis (45). Accordingly, the distancer (135) has a certain length in the direction of the central longitudinal axis (45) and the distancer (135) has accordingly the effect of keeping the outlet end (17) substantial parallel to the wall of the vessel or cavity in which the outlet end (17) is installed apart from maintaining the outlet end (17) with the outlet opening (19) at a minimum distance from the wall of said vessel or cavity and the endothelium thereof.

Figure 8:
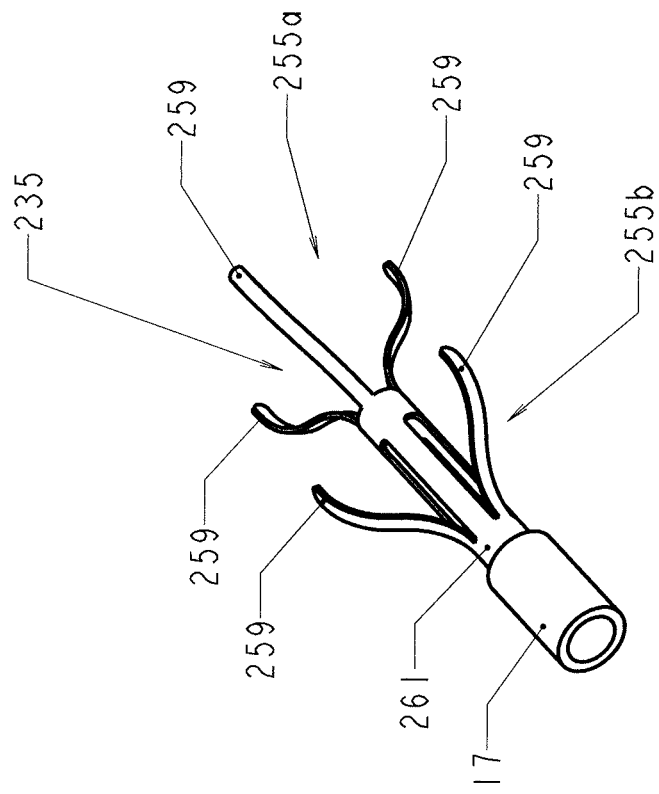
FIG. 8 is a view of the outlet end with a distancer in a third embodiment.

FIG. 8 shows in perspective a third embodiment of a distancer (235) according to the present invention. In this embodiment the distance members (239) are cut and formed from a tube (261) of a shape-memory alloy. The figure shows the distance member (239) in its use position which it will obtain when installed in a patient. A part of the tube (261) is inserted into the outlet opening (19) of the tubular outlet element (15) for the mounting of the distancer (235). The distancer (235) comprises two sets (255a) and (255b) of each three distance members (239a) and (239b). Like in the second embodiment the distance members (239a) and (239b) are curved, but in this embodiment the ends of the respective distance members protrude most from the central longitudinal axis (45) of the tubular outlet element (15) and accordingly these ends constitute distance keepers (259).

Like in the second embodiment the two sets (255a) and (255b) of distance members (239a) and (239b) are positioned at different distance from the outlet opening of the tubular outlet element and accordingly the outlet end thereof is kept substantially parallel to the wall of the vessel or cavity in which the outlet end with the distancer (235) is installed apart from the outlet end (17) with the outlet opening (19) being kept at a minimum distance from the wall of said vessel or cavity and the endothelium thereof.

It should be noted that correspondingly in the first embodiment the distancer (35) might be provided with two (or more) sets of distance members (39) in the form of resilient meshes attached to the outlet end (17) by means of respective attachment members (51) at different distances from the outlet opening (19) thereby obtaining for the first embodiment the effect of the outlet end (17) being kept substantially parallel to the wall of the vessel or cavity in which the outlet end (17) with such embodiment of the distancer is installed.

It should also be noted that although in the embodiment of the shunt devise described above the shunt body (3) comprises a flow restricting member (31), the flow restricting effect thereof might be obtained by a flow restricting part positioned elsewhere in the shunt device (1) between the inlet opening (11) and the outlet opening (19), e.g. in the third embodiment the tube (261) might provide or accommodate a flow restricting member providing the pursued resistance to the flow of the CSF through the shunt device in which case the flow restricting member of the shunt body might be eliminated.

Embodiments of the present invention are recited in the below-captioned items.

1. A shunt device comprising a tubular inlet element (7) having an inlet end (9) with an inlet opening (11) for insertion in a cerebrospinal fluid (CSF) containing space (13), such as a subarachnoid space or a brain ventricle, and a tubular outlet element (15) having an outlet end (17) with an outlet opening (19) adapted for insertion in a sinus system cavity (21), such as sinus transversus or vena jugularis, said tubular elements (7, 15) respectively comprising an inner lumen extending through the respective tubular element (7, 15), and said shunt device further comprising a flow restricting part (31) positioned between the inlet opening (9) and the outlet opening (19), the inner lumen of the tubular inlet element (7) and the inner lumen of the tubular outlet element (15) being connected for CSF to flow through the shunt device from the inlet opening (7) to the outlet opening (19), and the shunt device further comprises a one-way valve (33) preventing flow in a direction from the outlet opening to the inlet opening, characterized in that it further comprises a distancer (35; 135; 235), said distancer being provided at the outlet end (17) of the tubular outlet element (15) and comprising at least three distance keepers (43a; 59; 259) each being positioned at a distance from the tubular outlet element (15) in a direction perpendicular to a central longitudinal axis (45) of the tubular outlet element (15) at least in a use state of the shunt device.

2. A shunt device according to item 1, wherein each distance keeper forms part of a distance member protruding from the tubular outlet element in a direction away from the central longitudinal axis.

3. A shunt device according to item 1 or 2, wherein said at least three distance keepers are positioned equidistantly from each other at least when in a use state.

4. A shunt device according to one or more of the preceding items wherein said at least three distance keepers and/or distance members are positioned in a fashion satisfying the equation α+β+γ=360°, where α, β, and γ represents non-overlapping angles between two distance keepers and/or distance members when seen in the direction of the central longitudinal axis of the inner lumen, and where α>90°, β>90°, and γ>90°, and preferably α<150°, β<150°, and γ<150°.

5. A shunt device according to one or more of items 2-4, further comprising connector members each interconnecting two or more of the at least three distance members in order to hinder tangential movement of the distance members when seen in the direction of the central longitudinal axis.

6. A shunt device according to one or more of items 2-5, wherein the distancer comprises two or more sets of distance members and wherein the distance members of one set being arranged to protrude from the tubular outlet element at a different distances from the outlet opening in the direction of the central longitudinal axis than the distance members of another set.

7. A shunt device according to one or more of the preceding items, wherein the distancer comprises a resilient mesh comprising the at least three distance keepers defining the maximum protrusion of the mesh from the central longitudinal axis.

8. A shunt device according to one or more of the preceding items, wherein the distancer is connected to the tubular outlet element via one or more attachment members.

9. A shunt device according to one or more of the preceding items, wherein the distancer is compactable into a compacted state and expandable into at least one expanded use state where the at least three distance keepers protrude further from the central longitudinal axis than in the compacted state.

10. A shunt device according to any one of the preceding items, wherein the flow restricting part is a part of a shunt body and wherein the tubular inlet element further includes a brain ventricle catheter adapted for draining cerebrospinal fluid from a brain ventricle to the shunt body and the tubular outlet element includes a sinus catheter adapted for draining cerebrospinal fluid from the shunt body to the sinus system cavity.

11. Method for shunting cerebrospinal fluid using a shunt device according to one or more of the preceding items, the method comprising the steps of:
   a) inserting at least a part of the tubular inlet element, comprising the inlet opening, into a cerebrospinal fluid containing space, such as the subarachnoid space of a patient,
   b) inserting at least a part of the tubular outlet element, comprising the outlet opening and the distancer in a compacted state into a cavity of the sinus system, such as the sinus transversus or the vena jugularis cavity of the patient,
   c) changing the state of the distancer from the compacted state to an expanded use state, and
   d) fixating the shunt device.

12. Method of item 10, wherein the insertion of the tubular outlet element end in step b) is carried out through an opening in the vena jugularis.

13. Method of item 11 wherein the shunt device is fixated in a position where the distancer is at a distance of at least 3 cm, from the opening in the vena jugularis.

14. Use of a shunt device according to any one of items 1 to 10 in the treatment of hydrocephalus.

The invention claimed is:

1. A shunt device comprising
a a brain ventricle catheter comprising an inlet end with an inlet opening, and configured for insertion in a cerebrospinal fluid (CSF) containing space,
a sinus catheter comprising an outlet end with an outlet opening, and configured for insertion in a sinus system cavity,
a distancer attached at the outlet opening or at a distal portion of the outlet end of the sinus catheter, and configured to maintain the outlet end at an essentially fixed distance from endothelium tissue surrounding the sinus catheter when inserted into the sinus system cavity,
wherein each catheter comprises an inner lumen, and wherein the inner lumen of the catheters are operably connected through a shunt body to allow CSF to flow through the shunt device in the direction from the inlet opening to the outlet opening, wherein the shunt body comprises
a flow restricting part, and
a one-way valve configured to prevent CSF to flow in a direction from the outlet opening to the inlet opening.

2. The shunt device according to claim 1, wherein the distancer prevents the outlet end from contacting surrounding endothelium tissue when the the sinus catheter is inserted into the sinus system cavity.

3. The shunt device according to claim 1, wherein the outlet end is maintained substantially at a central position of a sinus system cavity, when the the sinus catheter is inserted into the sinus system cavity.

4. The shunt device according to claim 1, wherein the outlet end is maintained in a position substantially parallel to the flow direction of the sinus system cavity, into which the the sinus catheter is inserted.

5. The shunt device according to claim 1, wherein the direction of the flow of CSF exiting the outlet end is substantially parallel to the flow direction of the sinus system cavity, into which the the sinus catheter is inserted.

6. The shunt device according to claim 1, wherein the orientation of the outlet end is substantially parallel to the central, longitudinal axis of the distancer.

7. The shunt device according to claim 1, wherein the distancer is integral with the outlet end of the sinus catheter.

8. The shunt device according to claim 7, wherein said at least three distance keepers and/or distance members are positioned to satisfy the equation $\alpha+\beta+\gamma=360°$, where $\alpha$, $\beta$, and $\gamma$ represents non-overlapping angles between two distance keepers and/or distance members when seen in the direction of the central longitudinal axis of the sinus catheter, and where $\alpha>90°$, $\beta>90°$, and $\gamma>90°$.

9. The shunt device according to claim 7, further comprising connector members each interconnecting two or more of the at least three distance members in order to hinder tangential movement of the distance members when seen in the direction of the central longitudinal axis of the outlet end of the sinus catheter.

10. The shunt device according to claim 7, wherein the distancer comprises two or more sets of distance members, the distance members of one set being arranged to protrude from the sinus catheter at a different distance from the outlet opening than the distance members of another set, wherein each set is positioned in the direction of the central longitudinal axis of the outlet end of the sinus catheter.

11. The shunt device according to claim 1, wherein the distancer comprises at least three distance keepers, each being positioned at a distance from the sinus catheter in a direction perpendicular to a central longitudinal axis of the outlet end of the sinus catheter.

12. The shunt device according to claim 11, wherein each distance keeper forms part of a distance member protruding from the sinus catheter in a direction away from the central longitudinal axis.

13. The shunt device according to claim 11, wherein said at least three distance keepers are positioned equidistantly from each other.

14. The shunt device according to claim 1, wherein the distancer comprises a resilient mesh comprising at least three distance keepers defining the maximum protrusion of the mesh from the central longitudinal axis of the outlet end of the sinus catheter.

15. The shunt device according to claim 1, wherein the distancer is attached to the outlet end of the sinus catheter via one or more attachment members.

16. The shunt device according to claim 1, wherein the distancer is compactable into a compacted state, and expandable into at least one expanded state.

17. The shunt device according to claim 1, wherein the distancer comprises at least three distance keepers protruding from the central longitudinal axis of the outlet end of the sinus catheter.

18. A method for shunting cerebrospinal fluid using a shunt device according to claim 1, the method comprising the steps of:
 a) inserting at least the part of the brain ventricle catheter comprising the inlet opening into a cerebrospinal fluid containing space,
 b) inserting at least the part of the sinus catheter comprising the outlet opening and distancer into a cavity of the sinus system, where the distancer is in a compacted state,
 c) changing the state of the distancer from the compacted state to an expanded state, and
 d) fixating the shunt device.

19. The method of claim 18, wherein the cavity of the sinus system is the vena jugularis, and insertion of the sinus catheter in step b) is carried out through an opening in the vena jugularis.

20. The method of claim 19, wherein the outlet end of the sinus catheter is fixated in a position where the distancer is at a distance of at least 3 cm from the opening in the vena jugularis.

21. A method for fixating the shunt device according to claim 1 in a sinus system cavity of an individual, the method comprising the steps of:
 a) inserting at least the part of the brain ventricle cathether comprising the inlet opening into a cerebrospinal fluid containing space,
 b) inserting at least the part of the sinus catheter comprising the outlet opening and distancer into a cavity of the sinus system, where the distancer is in a compacted state,
 c) changing the state of the distancer from the compacted state to an expanded use state, and
 d) fixating the shunt device.

22. The method of claim 21, wherein the distancer prevents the outlet end of the sinus catheter from contacting surrounding endothelium tissue when the sinus catheter is inserted into the sinus system cavity.

23. The method of claim 21, wherein the outlet end of the sinus catheter is maintained substantially at a central position of the sinus system cavity when the sinus catheter is inserted into said sinus system cavity.

24. The method of claim 21, wherein the outlet end of the sinus catheter is maintained in a position substantially parallel to the flow direction of the sinus system cavity into which the sinus catheter is inserted.

25. The method of claim 21, wherein the direction of the flow of CSF exiting the outlet end of the sinus catheter is substantially parallel to the flow direction of the sinus system cavity into which the sinus catheter is inserted.

26. The method of claim 21, wherein the orientation of the outlet end of the sinus catheter is substantially parallel to the central, longitudinal axis of the distancer.

27. The method of claim 21, wherein the distancer is integral with the outlet end of the sinus catheter.

28. A shunt device comprising
 a brain ventricle catheter comprising an inlet end with an inlet opening,
 a sinus catheter comprising an outlet end with an outlet opening,
 a distancer attached at the outlet opening or at a distal portion of the outlet end of the sinus catheter,
 wherein each catheter comprises an inner lumen, and wherein the inner lumen of the catheters are operably connected through a shunt body, wherein the shunt body comprises
 a flow restricting part, and a one-way valve.

29. A shunt device comprising
 a brain ventricle catheter comprising an inlet end with an inlet opening,
 a sinus catheter comprising an outlet end with an outlet opening,
 a distancer attached to the outlet end of the sinus catheter and having a central longitudinal axis coaxial with the central longitudinal axis of the outlet end of the sinus catheter,
 wherein each catheter comprises an inner lumen, and wherein the inner lumen of the catheters are operably connected through a shunt body, wherein the shunt body comprises
 a flow restricting part, and a one-way valve.

* * * * *

UNITED STATES PATENT AND TRADEMARK OFFICE
CERTIFICATE OF CORRECTION

PATENT NO. : 10,625,060 B2  
APPLICATION NO. : 16/290753  
DATED : April 21, 2020  
INVENTOR(S) : Svend Erik Børgesen Page 1 of 1

It is certified that error appears in the above-identified patent and that said Letters Patent is hereby corrected as shown below:

On the Title Page

Item (30) Foreign Application Priority Data, insert:  
--Jun. 20, 2016 (WO) ............. PCT/EP2016/064145--

Signed and Sealed this  
Twenty-eighth Day of June, 2022

Katherine Kelly Vidal  
*Director of the United States Patent and Trademark Office*